US00PP18040P3

(12) United States Plant Patent
Mowrey et al.

(10) Patent No.: US PP18,040 P3
(45) Date of Patent: Sep. 18, 2007

(54) STRAWBERRY PLANT NAMED 'DRISCOLL SAUSALITO'

(50) Latin Name: *Fragaria×ananassa*
Varietal Denomination: Driscoll Sausalito

(75) Inventors: Bruce D. Mowrey, Watsonville, CA (US); Larry T. Kodama, Watsonville, CA (US); JoAnn Coss, Salinas, CA (US); Michael Ferguson, Moorpark, CA (US)

(73) Assignee: Driscoll Strawberry Associates, Inc.

( * ) Notice: Subject to any disclaimer, the term of this patent is extended or adjusted under 35 U.S.C. 154(b) by 0 days.

(21) Appl. No.: 11/271,762

(22) Filed: Nov. 10, 2005

(65) Prior Publication Data

US 2007/0107105 P1 May 10, 2007

(51) Int. Cl.
*A01H 5/00* (2006.01)

(52) U.S. Cl. ..... Plt./209

(58) Field of Classification Search ..... Plt./209, Plt./208
See application file for complete search history.

*Primary Examiner*—Kent Bell
*Assistant Examiner*—June Hwu
(74) *Attorney, Agent, or Firm*—Jones Day

(57) ABSTRACT

This invention relates to a new and distinct variety of strawberry named 'Driscoll Sausalito'. The variety is similar to the varieties 'Driscoll Lanai' and 'San Juan'. The variety is distinguished from 'Driscoll Lanai' and 'San Juan,' in particular, by its sweetness, acidity, internal color, longer petal length, longer flower diameter, anythocyanin color and coloration and moderate resistance to powdery mildew.

5 Drawing Sheets

Latin name of the genus and species of the plant claimed: The variety is botanically identified as *Fragaria×ananassa*.

Variety denomination: The strawberry variety denomination is 'Driscoll Sausalito'.

BACKGROUND OF THE INVENTION

The new variety originated as a result of a controlled cross between the strawberry plants 'San Juan' (U.S. Plant Pat. No. 12,899) and 14C185 (Unpatented Driscoll Variety) in an ongoing breeding program, and was discovered in Monterey County, Calif. in 2000. The original seedling of the new cultivar was asexually propagated by stolons in a Nursery in Shasta County, Calif. Propagules were transplanted to a controlled breeding plot in Monterey County, Calif., where the variety was identified and selected for further evaluation. 'Driscoll Sausalito' was subsequently asexually propagated and underwent further testing in Monterey County, Calif. for five years. This propagation and testing has demonstrated that the combination of traits disclosed herein which characterize the new variety are fixed and retained true to type through successive generations of asexual reproduction.

SUMMARY OF THE INVENTION

The present invention relates to a new and distinct variety of strawberry named 'Driscoll Sausalito'. The variety is botanically identified as *Fragaria×ananassa*. The new variety is distinguished from other varieties by a number of characteristics as set forth in Tables 1–4.

COMPARISON TO SIMILAR VARIETIES

The varieties which we believe to be similar to 'Driscoll Sausalito' from those known to us are 'Driscoll Lanai' (U.S. Plant Pat. No. 15,145) and 'San Juan' (U.S. Plant Pat. No. 12,899). There are several characteristics of the new variety that are different from, or not possessed by 'Driscoll Lanai' and 'San Juan'. For example, the new variety has a different internal color, longer petal length, longer flower diameter, different anythocyanin color and coloration and is moderately resistant to powdery mildew. Additional characteristics of 'Driscoll Sausalito' include an orbicular petal shape, a rounded petal apex and an obtuse petal base. The typical and observed petal number of 'Driscoll Sausalito' is six and the petal margin is entire. The typical and observed sepal number of 'Driscoll Sausalito' is ten. 'Driscoll Sausalito' also has a laceolate sepal shape, an acute sepal apex and a serrate sepal margin. 'Driscoll Sausalito' also has a typical and observed broadly obviate leaflet shape and an obtuse leaflet apex. The average number of strawberries on the fruiting truss of 'Driscoll Sausalito' is one.

'Driscoll Sausalito' is distinguished from its parent, 'San Juan' as indicated in Tables 1–4. Plants of 14C185 were not available for side by side comparison. 'Driscoll Sausalito' differs from 14C185 by having brighter red, more uniformly colored berries and superior shelf-life.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
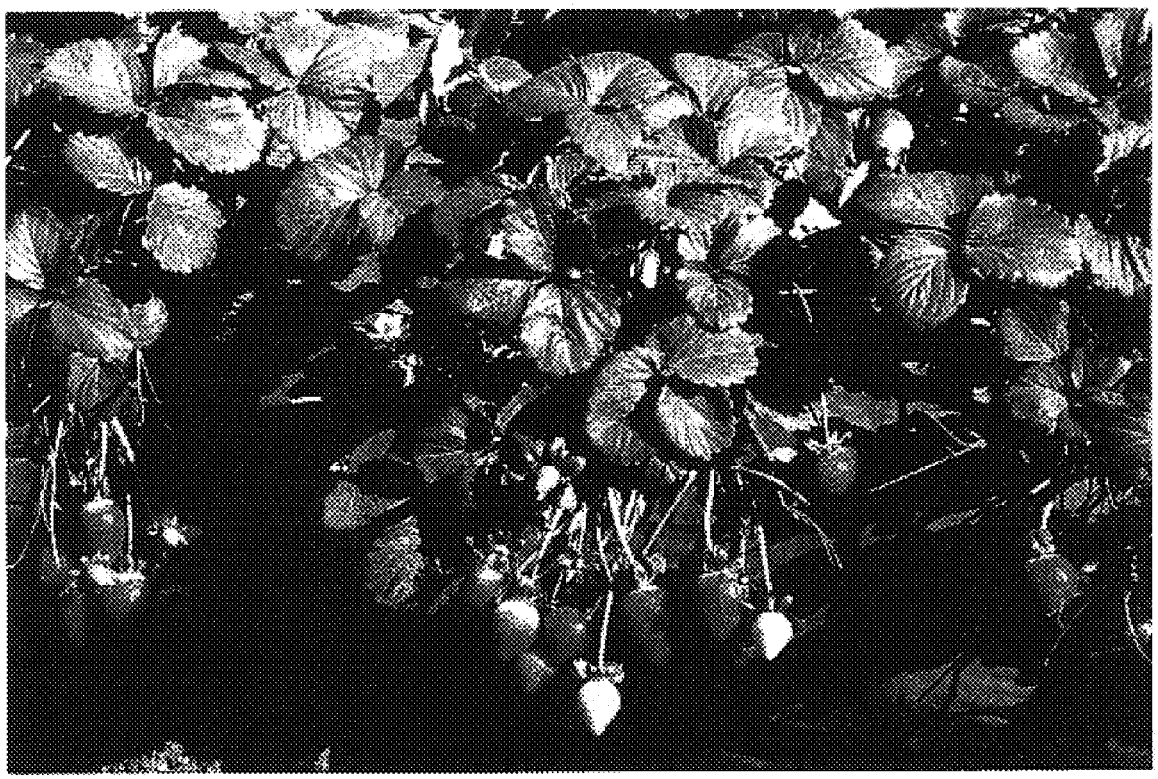
FIG. 1 shows the whole the plant.
Figure 2:
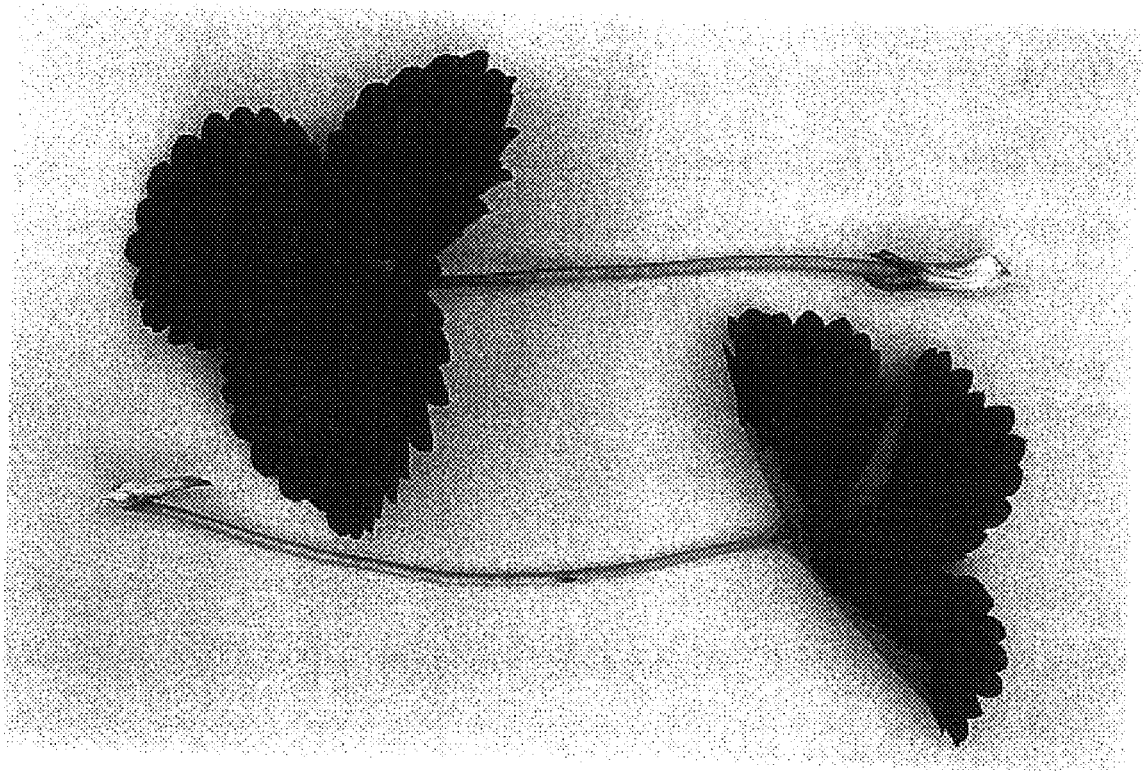
FIG. 2 shows the upper side of the leaves of the plant.
Figure 3:
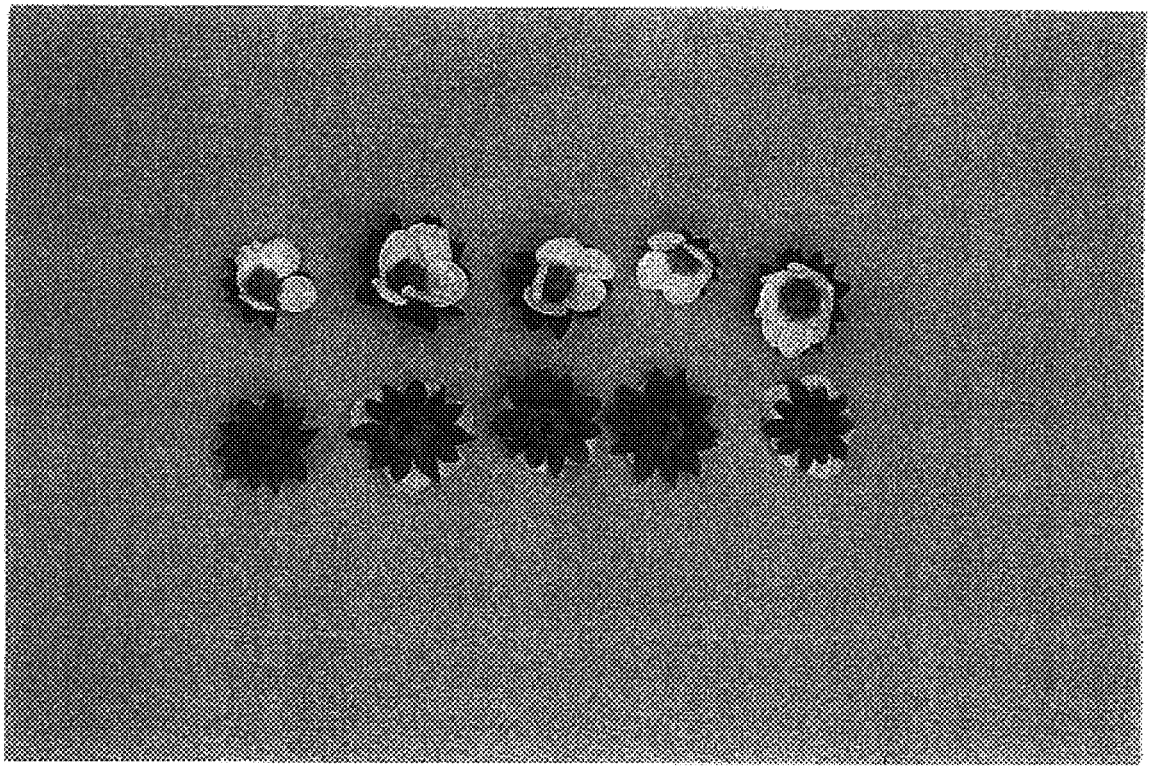
FIG. 3 shows the under side and upper side of the flowers.
Figure 4:
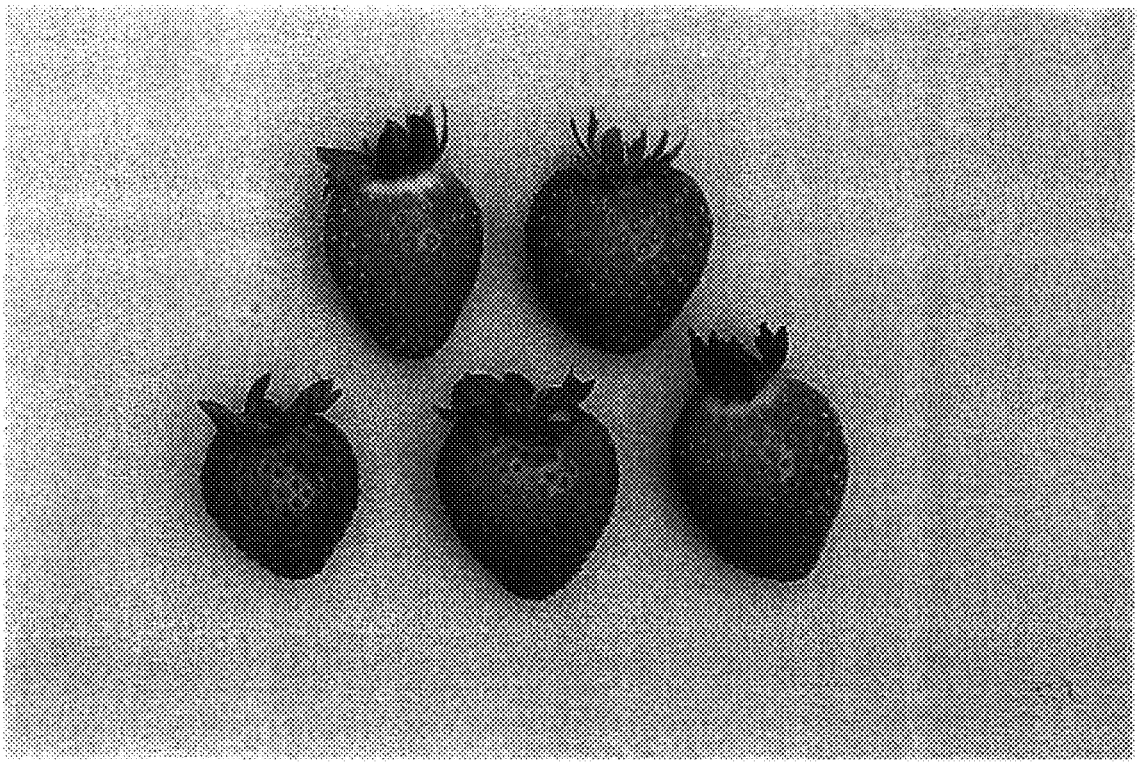
FIG. 4 shows a close-up of the fruit.
Figure 5:
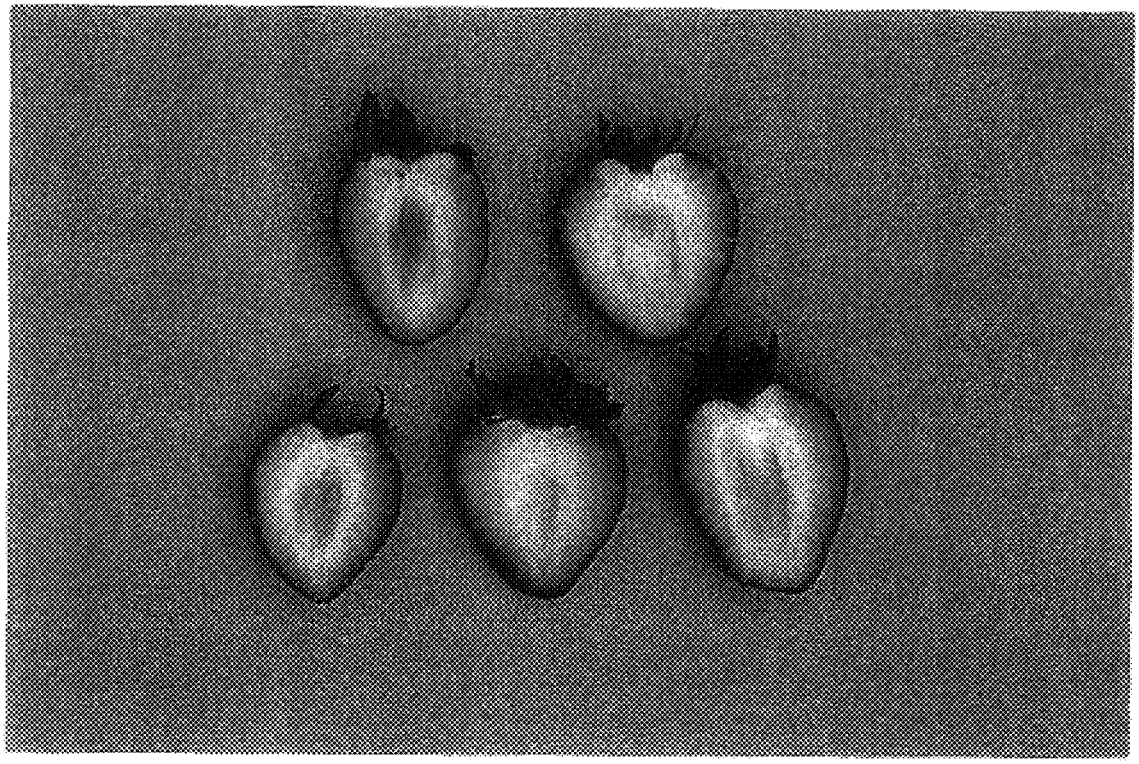
FIG. 5 shows the fruit in longitudinal cross-section.

The following detailed description of the new variety is based upon observations taken on plants harvested from a nursery in Shasta country, Calif. in October, 2004 and held in cold storage until planting in Monterey County, Calif. in November 2004. Plants were grown in raised beds of soil under conditions typical of commercial strawberry production in Monterey County, Calif. Observations of 'Driscoll Sausalito', 'Driscoll Lanai', and 'San Juan' were made in side by side comparison in July 2005. Fruits were harvested twice weekly from April, 2004 to November, 2004 for yield determination. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

PROPAGATION

The new variety is principally propagated by way of stolons. Although propagation by stolons is presently preferred, other known methods of propagating strawberry plants may be employed.

CHARACTERISTICS OF THE NEW VARIETY

Information on the new variety is presented in Tables 1, 2, 3 and 4. In the tables, the flowers described are secondary flowers except where indicated. The fruit described is the secondary fruit on seven month old plants. Fruit and flower measurements are an average of both primary and secondary fruit and flowers.

Table 1 provides information on the plant and fruit characteristics of the new variety 'Driscoll Sausalito' compared with characteristics of 'Driscoll Lanai' and 'San Juan'. Table 2 provides additional information of the plant and fruit characteristics of the new variety 'Driscoll Sausalito' compared with characteristics of the varieties 'Driscoll Lanai' and 'San Juan'. Table 3 provides reactions of the new variety to stresses, pests and diseases compared with reactions of the varieties 'Driscoll Lanai' and 'San Juan'. Table 4 provides isozyme characteristics of the new variety as compared to that of the varieties 'Driscoll Lanai' and 'San Juan'.

TABLE 1

QUANTITATIVE COMPARISON OF 'DRISCOLL SAUSALITO', 'DRISCOLL LANAI' AND 'SAN JUAN'

| | 'Driscoll Sausalito' | 'Driscoll Lanai' | 'San Juan' |
|---|---|---|---|
| Plant Characteristics | | | |
| Height of Plant (cm) | 24.7 | 23.4 | 28.9 |
| Spread of Plant (cm) | 45.6 | 38.3 | 51.7 |
| Number of Crowns | 3.5 | 3.3 | 4.3 |
| Leaf Characteristics | | | |
| Terminal Leaflet Length (cm) | 6.9 | 6.7 | 7.5 |
| Terminal Leaflet Width (cm) | 6.6 | 6.6 | 7.6 |
| Terminal Leaflet Length/Width Ratio | 1.04 | 1.00 | 0.99 |
| # Teeth/Terminal Leaflet | 17.8 | 21.1 | 20.4 |
| Color of upper side | 137A medium green | 139A medium green | 147A medium to dark green |
| Color of under side | 137C light green | 138B light green | 147C light green |
| Petiole Length (cm) | 19.4 | 18.0 | 25.7 |
| Petiole Diameter (mm) | 3.6 | 2.9 | 3.7 |
| Petiole Color | 145B yellow green | 145A yellow green | 149A yellow green |
| Petiolule Length (mm) | 8.0 | 10.7 | 7.5 |
| Petiolule Diameter (mm) | 1.8 | 1.7 | 2.1 |
| Petiolule Color | 145C yellow green | 145A yellow green | 149A yellow green |
| Bract Frequency | 8% typically single | 0% | 33% typically single |
| Stipule Length (cm) | 3.5 | 3.2 | 3.5 |
| Stipule Width (cm) | 0.9 | 0.8 | 0.7 |
| Stolon Characteristics | | | |
| Anthocyanin color | 185A greyed purple | 60A red purple | 59A red purple |
| Diameter at bract (mm) | 3.16 | 2.93 | 3.49 |
| Avg. # of Daughter plants (2003 Nursery) | 56 | 59 | 69 |
| Flower Characteristics | | | |
| Petal Length (cm) | 1.4 | 1.1 | 1.1 |
| Petal Width (cm) | 1.3 | 1.2 | 1.2 |
| Petal Length/Width Ratio | 1.08 | 0.94 | 0.90 |
| Flower Diameter (cm) | 3.1 | 2.8 | 2.6 |
| Calyx Diameter (cm) | 3.6 | 3.9 | 3.5 |
| Sepal Length (mm) | 11.4 | 11.7 | 11.7 |
| Sepal Width (cm) | 5.5 | 4.8 | 5.6 |
| Color of Upper Side of Petal | 155C white | 155C white | 155C white |
| Receptical Color | 154C yellow green | 154C yellow green | 154C yellow green |
| Anther Color | 13A yellow | 9A yellow | 9A yellow |
| Fruiting Truss Length (cm) | 25.3 | 25.3 | 33.1 |
| Fruit Characteristics | | | |
| Fruit Length (cm) | 3.8 | 3.8 | 3.9 |
| Fruit Width (cm) | 3.6 | 4.0 | 4.3 |
| Fruit Length/Width Ratio | 1.04 | 0.96 | 0.90 |
| Average Berry Weight (g) | 2.18 | 23.9 | 25.4 |
| External Color | 46A orange red | 45B orange red | 53A dark red |
| Internal Color | 35A whitish | 47C orange red | 44A red |
| Achene Coloration | 185A to 162B greyed purple to greyed yellow | 185B to 154B greyed purple to greyed yellow | 46B to 16A dark red to yellow |
| Achenes per berry | 195 | 292 | 304 |
| Achene weight (g) | 0.0006 | 0.0005 | 0.0006 |
| 2004 Marketable Yield (g/plant) | 1,283 | 1,377 | 984 |

TABLE 2

QUALITATIVE COMPARISON OF 'DRISCOLL SAUSALITO', 'DRISCOLL LANAI' AND 'SAN JUAN'

| | 'Driscoll Sausalito' | 'Driscoll Lanai' |
|---|---|---|
| Plant | | |
| Habit | flat | flat |
| Canopy Density | medium | open |
| Vigor | weak to medium | medium |
| Leaf | | |
| Shape in cross section | slightly concave | slightly concave to flat |
| Interveinal blistering | medium | medium |
| Glossiness | weak | weak |
| Number of leaflets | three only | three only |
| Terminal leaflet margin profile | revolute | revolute |
| Terminal leaflet shape of base | rounded | rounded |
| Terminal leaflet shape of teeth | rounded | rounded |
| Stipule pubescence | sparse | medium to dense |
| Petiole pubescence | sparse to medium | medium dense |
| Petiole pose of hairs | outward | downward |
| Stolon | | |
| Anthocyanin coloration | very strong | strong |
| Thickness | medium | medium to thick |
| Pubescence | very sparse | dense |
| Inflorescence | | |
| Position relative to foliage | beneath to level | level to above |
| Diameter of calyx relative to corolla on secondary flowers | larger | same size to larger |
| Diameter of inner calyx relative to outer on secondary flowers | larger | larger |
| Spacing of petals | overlapping | overlapping |
| Fruiting Truss | | |
| Attitude at first picking | prostrate | prostrate |
| Fruit | | |
| Predominant shape | conical | conical to ovoid |
| Difference in shapes between primary and secondary fruits | slight | slight |
| Band without achenes | medium | narrow to medium |
| Unevenness of surface | weak | weak |
| Evenness of color | slightly uneven | even |
| Glossiness | strong | strong |
| Insertion of achenes | level to above fruit surface | level with surface |
| Insertion of calyx | level to above | level |
| Pose of the calyx segments | spreading to reflexed | spreading to reflexed |
| Size of calyx in relation to fruit on secondary fruit | same size | smaller |
| Adherence of calyx | strong | strong |
| Firmness of flesh | medium | medium |
| Evenness of flesh color | slightly uneven | uneven |
| Distribution of flesh color | marginal and central | marginal and central |
| Hollow center size | small | medium |
| Sweetness | strong | medium |
| Texture when tasted | fine | fine |
| Acidity | weak to medium | medium |
| Time of First Flowering After Planting in 2005 | mid-February | mid-February |
| Harvest Interval in 2005 | early April to early November | late March to early November |
| Type of Bearing | partially everbearing | partially everbearing |

TABLE 2-continued

QUALITATIVE COMPARISON OF 'DRISCOLL SAUSALITO', 'DRISCOLL LANAI' AND 'SAN JUAN'

| | 'San Juan' |
|---|---|
| Plant | |
| Habit | globose to flat globose |
| Canopy Density | medium |
| Vigor | medium |
| Leaf | |
| Shape in cross section | flat to slightly convex |
| Interveinal blistering | medium to strong |
| Glossiness | weak to medium weak |
| Number of leaflets | sometimes more than 3 leaflets (approx. 17% of leaves) |
| Terminal leaflet margin profile | revolute to flat |
| Terminal leaflet shape of base | obtuse to rounded |
| Terminal leaflet shape of teeth | rounded |
| Stipule pubescence | medium |
| Petiole pubescence | medium |
| Petiole pose of hairs | outward to downward |
| Stolon | |
| Anthocyanin coloration | strong |
| Thickness | medium |
| Pubescence | medium |
| Inflorescence | |
| Position relative to foliage | beneath to level |
| Diameter of calyx relative to corolla on secondary flowers | larger |
| Diameter of inner calyx relative to outer on secondary flowers | same size |
| Spacing of petals | overlapping |
| Fruiting Truss | |
| Attitude at first picking | prostrate |
| Fruit | |
| Predominant shape | conical to almost cylindrical |
| Difference in shapes between primary and secondary fruits | moderate |
| Band without achenes | narrow |
| Unevenness of surface | medium |
| Evenness of color | even |
| Glossiness | very strong |
| Insertion of achenes | level with surface |
| Insertion of calyx | level |
| Pose of the calyx segments | spreading to reflexed |
| Size of calyx in relation to fruit on secondary fruit | same size |
| Adherence of calyx | strong |
| Firmness of flesh | firm |
| Evenness of flesh color | slightly uneven to even |
| Distribution of flesh color | marginal and central |
| Hollow center size | medium |
| Sweetness | medium to strong |
| Texture when tasted | medium |
| Acidity | medium |
| Time of First Flowering After Planting in 2005 | mid-February |

TABLE 2-continued

| QUALITATIVE COMPARISON OF 'DRISCOLL SAUSALITO', 'DRISCOLL LANAI' AND 'SAN JUAN' | |
|---|---|
| Harvest Interval in 2005 | late March to early November |
| Type of Bearing | partially everbearing |

TABLE 3

REACTIONS TO STRESS PESTS AND DISEASES FOR 'DRISCOLL SAUSALITO', 'DRISCOLL LANAI' AND 'SAN JUAN'

| | 'Driscoll Sausalito' | 'Driscoll Lanai' | 'San Juan' |
|---|---|---|---|
| Reaction to Pests | | | |
| *Tetranychus urticae* | susceptible | susceptible | moderately susceptible |
| *Lygus Hesperus* | susceptible | susceptible | susceptible |
| Reaction To Diseases | | | |
| Botrytis fruit rot | susceptible | susceptible | susceptible |
| Powdery mildew | moderately resistant | susceptible | susceptible |
| *Verticillium* wilt | moderately resistant | moderately resistant | susceptible |
| Strawberry Mottle Virus | moderately resistant | moderately resistant | moderately resistant |
| *Xanthomonas fragariae* | moderately susceptible | moderately susceptible | moderately susceptible |

ISOZYME ANALYSIS

In addition to the morphological description above, the new cultivar 'Driscoll Sausalito' has been analyzed to obtain an indication of its genetic makeup to provide further means for identifying the new variety and distinguishing it from other somewhat similar and/or related strawberry varieties. Specifically, leaf samples of 'Driscoll Sausalito', 'Driscoll Lanai' and 'San Juan' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL SAUSALITO', 'DRISCOLL LANAI' AND 'SAN JUAN'

| Locus | 'Driscoll Sausalito' | 'Driscoll Lanai' | 'San Juan' |
|---|---|---|---|
| PGI | A2 | A1 | A2 |
| LAP | B3 | B3 | B3 |
| PGM | C2 | C2 | C4 |

What is claimed:

1. A new and distinct variety of strawberry plant, substantially as shown and described.

* * * * *